(12) United States Patent
Liu et al.

(10) Patent No.: US 11,591,333 B2
(45) Date of Patent: Feb. 28, 2023

(54) SUBSTITUTED PYRROLO[2,3-D]PYRIMIDINES AS JANUS KINASE INHIBITORS

(71) Applicants: CINKATE PHARM TECH (SHANGHAI) CO.,LTD., Shanghai (CN); CINKATE PHARMACEUTICAL INTERMEDIATES CO., LTD., Shanghai (CN)

(72) Inventors: Na Liu, Shanghai (CN); Lixia Bao, Shanghai (CN); Zhepeng Wei, Shanghai (CN); Yufeng Zhou, Shanghai (CN); Bin Rong, Shanghai (CN); Lihui Zhao, Shanghai (CN); Fei Xiao, Shanghai (CN)

(73) Assignees: CINAKATE PHARM TECH (SHANGHAI) CO., LTD., Shanghai (CN); CINKATE PHARMACEUTICAL INTERMEDIATES CO., LTD., Shanghai (CN)

( * ) Notice: Subject to any disclaimer, the term of this patent is extended or adjusted under 35 U.S.C. 154(b) by 567 days.

(21) Appl. No.: 16/092,394

(22) PCT Filed: Feb. 22, 2017

(86) PCT No.: PCT/CN2017/074446
§ 371 (c)(1),
(2) Date: Oct. 9, 2018

(87) PCT Pub. No.: WO2017/143990
PCT Pub. Date: Aug. 31, 2017

(65) Prior Publication Data
US 2022/0017522 A1    Jan. 20, 2022

(30) Foreign Application Priority Data
Feb. 23, 2016   (CN) .......................... 201610100165.5

(51) Int. Cl.
*A61K 31/519* (2006.01)
*C07D 487/04* (2006.01)

(52) U.S. Cl.
CPC .................. *C07D 487/04* (2013.01)

(58) Field of Classification Search
CPC ..................... A61K 31/519; C07D 487/04

USPC ....................................... 514/265.1; 544/280
See application file for complete search history.

(56) References Cited

U.S. PATENT DOCUMENTS

| 3,037,980 A | 6/1962 | Hitchings et al. |
| 7,687,507 B2 * | 3/2010 | Blumenkopf ........ C07D 487/04 544/280 |
| 2014/0073626 A1 | 3/2014 | Goldstein et al. |

FOREIGN PATENT DOCUMENTS

| CN | 103502249 A | 1/2014 |
| CN | 105732636 | * 7/2016 |
| WO | 99/65909 | 12/1999 |
| WO | 2014/015107 | 1/2014 |

OTHER PUBLICATIONS

International Search Report and Written Opinion; International Patent Application No. PCT/CN2017/074446, dated May 25, 2017 with English translation (16 pages).

* cited by examiner

*Primary Examiner* — Douglas M Willis
(74) *Attorney, Agent, or Firm* — Hamre, Schumann, Mueller & Larson, P.C.

(57) ABSTRACT

The present invention provides a method for preparing a pyrrolopyrimidine compound and application thereof. Specifically, the present invention provides a compound represented by formula I or pharmaceutically-acceptable salts thereof, a pharmaceutical composition containing the compound or its salts, and a method for preparing the pharmaceutical composition and an application of the pharmaceutical composition as an immunosuppressive drug.

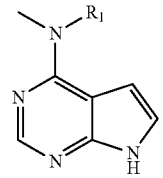

AA Formula I

10 Claims, No Drawings

SUBSTITUTED PYRROLO[2,3-D]PYRIMIDINES AS JANUS KINASE INHIBITORS

FIELD OF THE INVENTION

The present invention involves a method for preparing a pyrrolopyrimidine compound or pharmaceutically-acceptable salts thereof, a pharmaceutical composition containing the compound or its salts, and a method for preparing the pharmaceutical composition and an application of the pharmaceutical composition as an immunosuppressive drug.

BACKGROUND OF THE INVENTION

JAK1 plays a key role in a variety of cytokine and growth factor signaling pathways. Dysregulation of JAK1 would cause or contribute to disease or lead to inflammatory responses. For example, in rheumatoid arthritis, activation of interleukin 6 is of pro-inflammatory effect, while antagonism of IL-6 directly or indirectly by JAK1 inhibition will provide clinical benefit.

To other JAK kinases, selective inhibitors to JAK1 are of multiple therapeutic benefits when compared to less selective inhibitors. Regarding to the selectivity of JAK2, a variety of important cytokines and growth factors transmit signals through JAK2, including, for example, erythropoietin (EPO) and thrombopoietin (TPO). Reduced TPO signaling will lead to megakaryocyte reduction and may lead to thrombocytopenia. For the selectivity of JAK3, children with JAK3 kinase deficiency may have severe combined immunodeficiency disease. The compounds of the invention are JAK inhibitors, and most of the compounds of the invention are JAK1 selective inhibitors. JAK1 selective inhibitors are compounds that preferably inhibit JAK1 activity relative to other Janus kinases.

Therefore, there is an urgent need in the art to develop a compound having specific immunosuppressive activity.

SUMMARY OF THE INVENTION

The object of the present invention is to provide a structurally novel JAK1 enzyme selective inhibitor, and the preparation method and application thereof.

In the first aspect of the present invention, a compound of formula I, or a pharmaceutically acceptable salt thereof is provided,

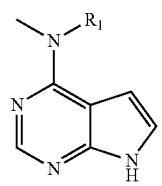

Formula I wherein, $R_1$ is selected from the group consisting of H, substituted or unsubstituted C1-C10 alkyl, substituted or unsubstituted C6-C10 aryl, substituted or unsubstituted C3-C10 cycloalkyl, substituted or unsubstituted C4-C10 heterocyclic group, substituted or unsubstituted C1-C10 heteroaryl group, —$R_aC(O)R_b$, —$R_1'$—$NR_cC(O)R_b$, and —$R_1'$—N=$CR_cR_b$; and the substitution means having one or more substituents selected from the group A1 consisting of substituted or unsubstituted C1-C10 alkyl, substituted or unsubstituted C6-C10 aryl, substituted or unsubstituted C3-C10 cycloalkyl, substituted or unsubstituted C4-C10 heterocyclic group, substituted or unsubstituted C1-C10 heteroaryl, halogen, —$NH_2$, —OH and —CN;

each $R_a$ and $R_b$ is independently selected from the group consisting of hydrogen, —CN, substituted or unsubstituted C1-C8 alkyl, substituted or unsubstituted C2-C8 alkenyl, substituted or unsubstituted C3-C8 alkynyl, substituted or unsubstituted C6-C10 aryl group, substituted or unsubstituted C3-C10 cycloalkyl group, substituted or unsubstituted C4-C10 heterocyclic group, and substituted or unsubstituted C1-C10 heteroaryl group, and the substitution means having one or more substituents selected from the group A2 consisting of halogen, amino, nitro, —OH, —CN, C1-C4 alkyl and C1-C4 haloalkyl;

$R_c$ is H or C1-C3 alkyl group;

$R_1'$ is phenyl or cyclohexyl;

wherein the C4-C10 heterocyclic group and the C1-C10 heteroaryl group each independently has 1 to 3 hetero atoms selected from N, O and S.

In another preferred embodiment, $R_b$ is a substituted or unsubstituted C1-C8 alkyl, a substituted or unsubstituted C2-C8 alkenyl, or a substituted or unsubstituted C4-C10 heterocyclic group, and the substitution means having one or more substituents selected from the group A4 consisting of halogen, —OH, —CN; the C4-C10 heterocyclic group has 1-3 heteroatoms selected from N, O and S.

In another preferred embodiment, the formula I compound is selected from the following formula I-b or I-c compound:

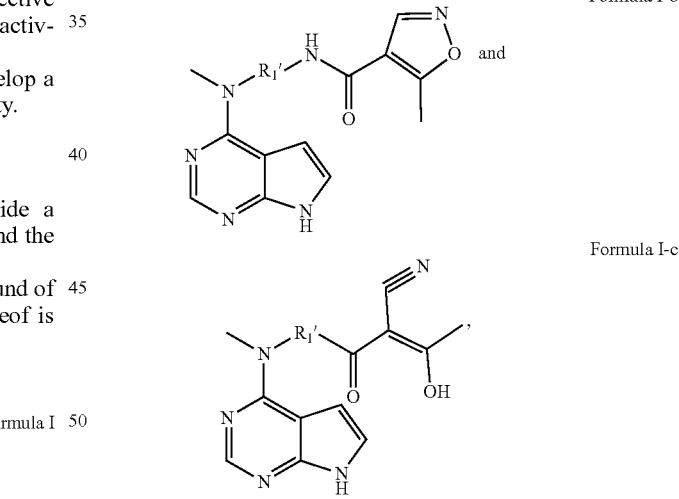

wherein $R_1$, $R_1'$ are as defined above.

In another preferred embodiment, the compound of formula I is selected from the group consisting of:

N-methyl-N-(7H-pyrrolo[2,3-d]pyrimidin-4-yl)phenyl-1,4-diamine;

5-methyl-isoxazole-{4-[methyl-(7H-pyrrolo[2,3-d]pyrimidin-4-yl)-amino]-phenyl}-4-amide;

5-methyl-isoxazole-{4-[methyl-(7H-pyrrolo[2,3-d]pyrimidin-4-yl)-amino]-cyclohexyl}-amine;

2-cyano-3-hydroxy-2-butene-{4-[methyl-(7H-pyrrolo[2,3-d]pyrimidin-4-yl)-amino]-phenyl]-amide;

2-cyano-3-hydroxy-2-butene-{4-[methyl-(7H-pyrrolo[2,3-d]pyrimidin-4-yl)-amino]-cyclohexyl]-amide; and 3-hydroxy-2-(1-{4-[methyl-(7H-pyrrolo[2,3-d]pyrimidin-4-yl)-amino]-iminophenyl}-ethyl)-2-butenenitrile.

In the second aspect of the present invention, a method for the preparation of compound of formula I-b is provided, which comprises

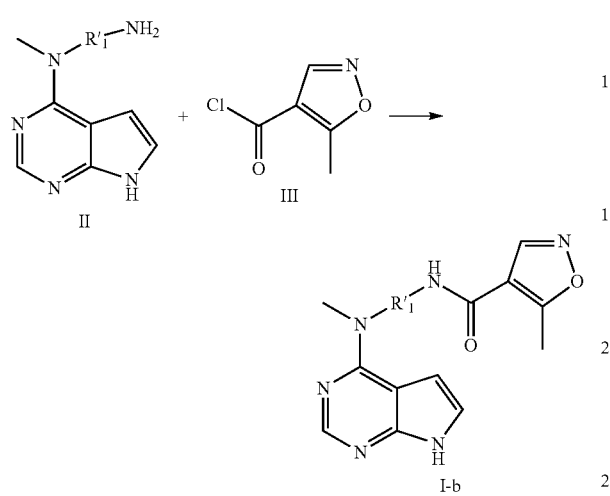

In an inert solvent, reacting formula II compound and formula III compound to obtain formula I-b compound, wherein the $R_1'$ is defined as above.

In another preferred embodiment, the inert solvent is selected from the group consisting of dichloromethane, chloroform, 1,2-dichloroethane, toluene, xylene, or the combinations thereof.

In another preferred embodiment, the molar ratio of the formula II compound to the formula III compound is 0.5-2:0.5-2, preferably about 1:1.

In another preferred embodiment, the reaction time of the process is 1-15 h, preferably 2-10 h, more preferably 0.5-5 h.

In another preferred embodiment, the reaction is carried out in the presence of organic base catalyst.

In another preferred embodiment, the organic base catalyst is selected from the group consisting of dimethylaminopyridine (DMAP), diisopropylethylamine (DIPEA), or the combinations thereof.

In another preferred embodiment, the reaction is carried out under catalysis of acid.

In another preferred embodiment, the acid catalyst is acid-binding agent.

In another preferred embodiment, the acid-binding agent is selected from the group consisting of triethylamine, pyridine, diethylamine, piperidine, or the combinations thereof.

In another preferred embodiment, the method further comprises the step (1-1): dissolving the compound of the formula II, the organic base, and the acid-binding agent in an inert solvent under −50 to 0° C., and dropping the formula III compound for reaction.

In another preferred embodiment, the step further comprises the step (1-2): heating the mixture obtained in the step (1-1) to room temperature for reaction.

In another preferred embodiment, the step further comprises the step (1-3): quenching the reaction with water.

In the third aspect of the present invention, a method for the preparation of a compound of formula I-c is provided, which comprises:

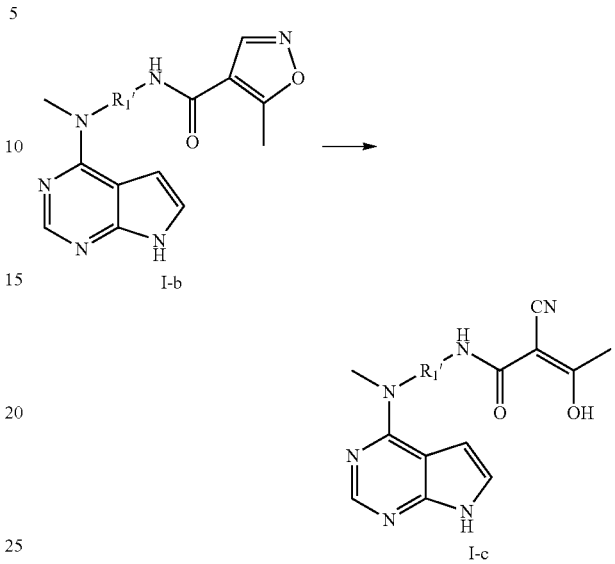

In an inert solvent, conducting ring-opening reaction to formula I-b compound so as to obtain formula I-c compound, wherein the $R_1'$ is defined as above.

In another preferred embodiment, the inert solvent is selected from the group consisting of toluene, dioxane, THF, or the combinations thereof.

In another preferred embodiment, the reaction is carried out under alkali condition.

In another preferred embodiment, the alkali is selected from the group consisting of potassium carbonate, sodium carbonate, sodium hydrogencarbonate, potassium hydrogencarbonate, or the combinations thereof.

In the fourth aspect of the present invention, a pharmaceutical composition is provided, comprising one or more of therapeutically effective amount of compound of the first aspect of the invention, or the pharmaceutically acceptable salt thereof, and a pharmaceutically acceptable excipient.

In the fifth aspect of the present invention, the use of a compound of the first aspect of the present invention, or a pharmaceutically acceptable salt thereof, or a pharmaceutical composition of the fourth aspect of the present invention in the preparation of a medicine for the prevention or treatment of JAK kinase related diseases, or the preparation of JAK kinase inhibitors is provided.

In another preferred embodiment, the JAK kinase is selected from the group consisting of JAK1, JAK2, and JAK3 kinase.

In another preferred embodiment, the disease is an autoimmune disease or chronic inflammatory disease.

In another preferred embodiment, the disease is selected from the group consisting of systemic lupus erythematosus, rheumatoid arthritis, multiple sclerosis, type II diabetes, inflammatory bowel disease, biliary cirrhosis, uveitis, Crohn's disease, ulcerative colitis, bullous pemphigoid, sarcoidosis, psoriasis, psoriatic arthritis, autoimmune myositis, Wegener's granulomatosis, Graves' eye disease, allergies dermatitis and asthma.

In the sixth aspect of the present invention, a method for non-therapeutic inhibition of JAK kinase activity is provided, which comprises the step: contacting a compound of the first aspect of the invention or a pharmaceutically acceptable salt thereof with JAK kinase so as to inhibit JAK kinase.

In the seventh aspect of the present invention, a method for inhibiting JAK kinase activity or treating JAK kinase related disease is provided, comprising the step: contacting a compound of the first aspect of the invention or a pharmaceutically acceptable salt thereof with JAK kinase so as to inhibit JAK kinase.

In another preferred embodiment, the method comprises administering a therapeutically effective amount of compound of the first aspect of the invention or a pharmaceutically acceptable salt thereof, or administering an therapeutically effective amount of pharmaceutical composition of the fourth aspect of the invention to a mammal in need.

It should be understood that, in the present invention, each of the technical features specifically described above and below (such as those in the Examples) can be combined with each other, thereby constituting new or preferred technical solutions which need not be specified again herein.

EMBODIMENTS FOR CARRYING OUT THE INVENTION

After long-term and intensive research, the present inventors have for the first time unexpectedly discovered a compound of the formula I or a pharmaceutically acceptable salt thereof which has an immunosuppressive activity, and can be used for the treatment of an immune-related disease. The present invention is completed on this basis.

Terms

Unless otherwise defined, all technical and scientific terms used herein have the same meaning as commonly understood by one of ordinary skill in the art to which this invention belongs.

As used herein, when used in a particular recited value, the term "about" means that the value can vary by no more than 1% from the recited value. For example, as used herein, the expression "about 100" includes all the values between 99 and 101 and (e.g., 99.1, 99.2, 99.3, 99.4, etc.).

As used herein, the terms "containing" or "including (comprising)" may be opened form, semi-closed form, or closed form. In other words, the terms also include situations such as "essentially consisting of . . . " or "consisting of . . . " As used herein, the "substituted" means that one or more hydrogen atoms of the group are substituted by substituents selected from the group consisting of halogen, amino, nitro, and C1-C4 alkyl.

In the present application, as a group or part of another group (for example, used in a group such as a halogen-substituted alkyl group), the term "alkyl" means a fully saturated straight or branched hydrocarbon chain group which consists only of carbon atoms and hydrogen atoms, and has, for example, 1 to 12 (preferably 1 to 8, more preferably 1 to 6) carbon atoms, and is bonded to the rest of the molecule by a single bond, for example, including but not limited to, methyl, ethyl, n-propyl, isopropyl, n-butyl, isobutyl, sec-butyl, tert-butyl, n-pentyl, 2-methylbutyl, 2,2-dimethylpropyl, n-hexyl, heptyl, 2-methylhexyl, 3-methylhexyl, octyl, decyl and decyl. Term "C3-C10 cycloalkyl" refers to cycloalkyls with 3 to 10 carbon atoms, such as cyclopropyl, cyclobutyl, cyclopentyl, cycloheptyl, or the like.

In the present application, as a group or part of another group, the term "alkenyl" means a straight or branched hydrocarbon chain group consisted only of carbon atoms and hydrogen atoms, containing at least one double bond, and having for example 2 to 14 (preferably 2 to 10, more preferably 2 to 6) carbon atoms and attached to the remaining part of the molecule by a single bond, e.g., but not limited to, vinyl, propenyl, allyl, but-1-enyl, but-2-enyl, pent-1-enyl, pentane-1,4-dienyl, and the like.

In the present application, as a group or part of another group, the term "alkynyl" means a straight or branched hydrocarbon chain group consisted only of carbon atoms and hydrogen atoms, containing at least one triple bond (optionally containing at least one double bond), and having for example, 2 to 14 (preferably 2 to 10, more preferably 2 to 6) carbon atoms and attached to the remaining part of the molecule by a single bond, such as, but not limited to, ethynyl, prop-1-ynyl, but-1-ynyl, pent-1-en-4-ynyl, and the like.

In the present application, as a group or part of another group, the term "heterocyclyl" means a stable 3- to 20-membered non-aromatic cyclic group consisted of 2 to 14 carbon atoms and 1 to 6 heteroatoms selected from the group consisting of nitrogen, phosphorus, oxygen and sulfur. Unless otherwise specifically indicated in the specification, heterocyclic group may be monocyclic, bicyclic, tricyclic or ring system with ever more cyclic, which may include fused ring system, bridged ring system or spiro ring system; the nitrogen, carbon or sulfur atom may optionally be oxidized; the nitrogen atom may optionally be quaternized; and the heterocyclic group may be partially or fully saturated. The heterocyclic group may be bonded to the remaining part of the molecule via a carbon atom or a hetero atom through a single bond. In the heterocyclic group containing a fused ring, one or more of the rings may be aryl or heteroaryl group as defined hereinafter, provided that the point of attachment to the rest part of the molecule is a non-aromatic ring atom. For the purposes of the present invention, the heterocyclic group is preferably a stable 4 to 11 membered non-aromatic monocyclic, bicyclic, bridged or spiro group containing from 1 to 3 heteroatoms selected from nitrogen, oxygen and sulfur. More preferably, it is a stable 4- to 8-membered non-aromatic monocyclic, bicyclic, bridged or spiro group containing from 1 to 3 heteroatoms selected from nitrogen, oxygen and sulfur. Examples of heterocyclic groups include, but are not limited to, pyrrolidinyl, morpholinyl, piperazinyl, homopiperazinyl, piperidinyl, thiomorpholinyl, 2,7-diaza-spiro[3.5]nonane-7-yl, 2-oxa-6-aza-spiro[3.3]heptane-6-yl, 2,5-diaza-bicyclo[2.2.1]heptan-2-yl, aza-cyclobutane, pyranyl, tetrahydropyranyl, thiapyranyl, tetrahydrofuranyl, oxazinyl, dioxocyclopentyl, tetrahydroisoquinolinyl, decahydroisoquinolinyl, imidazolinyl, imidazolidinyl, quinazolidinyl, thiazolidinyl, isothiazolidinyl, isoxazolidinyl, dihydroindolyl, octahydroindolyl, octahydroisodolyl, pyrrolidinyl, pyrazolidinyl, phthalimidoyl and the like.

In the present application, as a group or part of another group, the term "aryl" means a conjugated hydrocarbon ring system group having 6 to 18 carbon atoms, preferably having 6 to 10 carbon atoms. For the purposes of the present invention, an aryl group may be a monocyclic, bicyclic, tricyclic or ring system of even more cyclic, and may also be fused to a cycloalkyl or heterocyclic group as defined above, provided that the aryl group connected to the rest of the molecule by a single bond via atoms on the aromatic ring. Examples of aryl groups include, but are not limited to, phenyl, naphthyl, anthracenyl, phenanthryl, anthryl, 2,3-dihydro-1H-isoindolyl, 2-benzoxazolinone, 2H-1,4-benzoxazine-3(4H)-keto-7-yl, and the like. The term "C6-C10 aryl" refers to aryls with 6 to 10 carbon atoms, such as monocyclic or bicyclic aryl, such as phenyl, naphthyl, or the like.

In the present application, as a group or part of another group, the term "heteroaryl" means a conjugated hydrocarbon ring system group having 1 to 15 carbon atoms (preferably having 1 to 10 carbon atoms) and 1 to 6 heteroatoms selected from nitrogen, oxygen and sulfur. Unless otherwise indicated in the present invention, a heteroaryl group may be a monocyclic, bicyclic, tricyclic or ring system of even more cyclic, and may also be fused to a cycloalkyl or heterocyclic group as defined above, provided that the aryl group connected to the rest of the molecule by a single bond via atoms on the aromatic ring. The nitrogen, carbon or sulfur atom in the heteroaryl group can be optionally oxidized; and the nitrogen atom can optionally be quaternized. For the purposes of the present invention, the heterocyclic group is preferably a stable 5 to 12 membered aromatic group containing from 1 to 5 heteroatoms selected from nitrogen, oxygen and sulfur. More preferably, it is a stable 5- to 10-membered aromatic group containing from 1 to 3 heteroatoms selected from nitrogen, oxygen and sulfur, or 5- to 6-membered aromatic group containing from 1 to 3 heteroatoms selected from nitrogen, oxygen and sulfur Examples of heteroaryl groups include, but are not limited to, thienyl, imidazolyl, pyrazolyl, thiazolyl, oxazolyl, oxadiazolyl, isoxazolyl, pyridyl, pyrimidinyl, pyrazinyl, pyridazinyl, benzimidazolyl, benzopyrazolyl, indolyl, furyl, pyrrolyl, triazolyl, tetrazolyl, triazinyl, indolizinyl, isoindolyl, indazolyl, isoindazolyl, purinyl, quinolyl, isoquinolyl, diazonaphthyl, naphthyridinyl, quinoxalinyl, pteridinyl, carbazolyl, carboline, phenanthridinyl, phenanthrolinyl, acridinyl, phenazinyl, isothiazolyl, benzothiazolyl, benzothienyl, oxatriazole, cinnolinyl, quinazolinyl, phenylthio, purrocolinyl, orthophenanthrolenyl, isoxazolyl, phenoxazinyl, phenothiazine, 4,5,6,7-tetrahydrobenzo[b]thienyl, naphthopyridyl, [1,2,4]triazolo[4,3-b]pyridazine, [1,2,4]triazolo[4,3-a]pyrazine, [1,2,4]triazolo[4,3-c]pyrimidine, [1,2,4]triazolo[4,3-a]pyridine, imidazo[1,2-a]pyridine, imidazo[1,2-b]pyridazine, imidazo[1,2-a]pyrazine, etc. The term "C1-C10 heteroaryl" refers to heteroaryl with 1 to 10 carbon atoms, such as pyrrolyl, pyridyl, furyl, oxazolyl, or the like.

The term "halogen" refers to F, Cl, Br and I.

Certain chemical groups defined herein are preceded by a simplified symbol to indicate the total number of carbon atoms present in the group. For example, C1-C6 alkyl refers to an alkyl group as defined below having a total of from 1 to 6 carbon atoms. The total number of carbon atoms in the simplified symbol does not include carbon that may be present in the substituents of the group.

In the present application, the term "pharmaceutically acceptable salt" includes pharmaceutically acceptable acid addition salts and pharmaceutically acceptable base addition salts.

"Pharmaceutically acceptable acid addition salt" means a salt formed with an inorganic or organic acid which retains the bioavailability of the free base without bringing other side effects. Inorganic acid salts include, but are not limited to, hydrochlorides, hydrobromides, sulfates, nitrates, phosphates, and the like; organic acid salts include, but are not limited to, formate, acetate, 2,2-dichloroacetate, trifluoroacetate, propionate, hexanoate, octoate, decanoate, undecylenate, glycolate, gluconate, lactate, sebacate, adipates, glutaric acid salts, malonates, oxalates, maleates, succinates, fumarates, tartrates, citrates, palmitates, stearates, oleates, cinnamate, laurate, malate, glutamate, pyroglutamate, aspartate, benzoate, methanesulfonate, besylate, p-toluenesulfonate, alginate, ascorbate, salicylate, 4-aminosalicylate, naphthalene disulfonate, and the like. These salts can be prepared by methods known in the art.

"Pharmaceutically acceptable base addition salt" means a salt formed with an inorganic or organic base capable of maintaining the bioavailability of the free acid without bringing other side effects. Salts derived from inorganic bases include, but are not limited to, sodium salts, potassium salts, lithium salts, ammonium salts, calcium salts, magnesium salts, iron salts, zinc salts, copper salts, manganese salts, aluminum salts, and the like. Preferred inorganic salts are ammonium, sodium, potassium, calcium and magnesium salts. Salts derived from organic bases include, but are not limited to, the following salts: primary amines, secondary amines and tertiary amines, substituted amines, including naturally substituted amines, cyclic amines, and basic ion exchange resins. For example, ammonia, isopropylamine, trimethylamine, diethylamine, triethylamine, tripropylamine, ethanolamine, diethanolamine, triethanolamine, dimethylethanolamine, 2-dimethylaminoethanol, 2-diethylaminoethanol, bicyclo hexylamine, lysine, arginine, histidine, caffeine, procaine, choline, betaine, ethylenediamine, glucosamine, methylglucosamine, theobromine, purine, piperazine, piperidine, N-ethylpiperidine, polyamine resin, and the like. Preferred organic bases include isopropylamine, diethylamine, ethanolamine, trimethylamine, dicyclohexylamine, choline, and caffeine. These salts can be prepared by methods known in the art.

Pharmaceutical Composition and Method for Administration Thereof

In the present application, "pharmaceutical composition" refers to a formulation of a compound of the invention and a medium generally accepted in the art for delivery of a biologically active compound to a mammal, such as a human. The medium comprises pharmaceutically acceptable carriers. The purpose of the pharmaceutical composition is to promote the administration of the organism, thus facilitating the absorption of the active ingredients and thereby exerting the biological activity.

The term "pharmaceutically acceptable" as used herein, refers to a substance (such as a carrier or diluent) that does not affect the biological activity or properties of the compound of the invention, and is relatively non-toxic, i.e., the substance can be administered to an individual without causing undesirable biological response, or interacts with any of the components contained in the composition in an undesirable manner.

In the present application, "pharmaceutically acceptable excipients" include, but are not limited to, any adjuvants, carriers, excipients, glidants, sweeteners, diluents, preservatives, dyes/colorants, flavoring agents, surfactants, wetting agents, dispersing agents, suspending agents, stabilizers, isotonic agents, solvents or emulsifiers approved by the relevant government authorities for acceptable use in humans or domestic animals.

In the present invention, the term "effective amount" refers to an amount in which the therapeutic agents can treat, relieve or prevent the targeted disease, or exhibit detectable treatment or prevention effects. The exact effective amount for a subject will depend on the size and health condition of the subject, the nature and extent of the disorder, and the therapeutic agent and/or therapeutic agent combination selected for administration. Therefore, it is useless to specify an accurate effective amount in advance. However, for a given situation, the effective amount may be determined by routine experimentation, which can be determined by clinicians.

Compound of Formula I

As described by the present invention, a compound of formula I, or the pharmaceutically acceptable salts thereof,

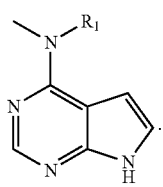

Formula I wherein,

R$_1$ is selected from the group consisting of H, substituted or unsubstituted C1-C10 alkyl, substituted or unsubstituted C6-C10 aryl, substituted or unsubstituted C3-C10 cycloalkyl, substituted or unsubstituted C4-C10 heterocyclic group, substituted or unsubstituted C1-C10 heteroaryl group, —R$_a$C(O)R$_b$, —R$_1$'—NR$_c$C(O)R$_b$, and —R$_1$'—N=CR$_c$R$_b$; and the substitution means having one or more substituents selected from the group A1, consisting of substituted or unsubstituted C1-C10 alkyl, substituted or unsubstituted C6-C10 aryl, substituted or unsubstituted C3-C10 cycloalkyl, substituted or unsubstituted C4-C10 heterocyclic group, substituted or unsubstituted C1-C10 heteroaryl, halogen, —NH$_2$, —OH and —CN;

each R$_a$ and R$_b$ is independently selected from the group consisting of hydrogen, —CN, substituted or unsubstituted C1-C8 alkyl, substituted or unsubstituted C2-C8 alkenyl, substituted or unsubstituted C3-C8 alkynyl, substituted or unsubstituted C6-C10 aryl group, substituted or unsubstituted C3-C10 cycloalkyl group, substituted or unsubstituted C4-C10 heterocyclic group, and substituted or unsubstituted C1-C10 heteroaryl group, and the substitution means having one or more substituents selected from the group A2, consisting of halogen, amino, nitro, —OH, —CN, C1-C4 alkyl and C1-C4 haloalkyl;

R$_c$ is H or C1-C3 alkyl group;

R$_1$' is phenyl or cyclohexyl;

Wherein the C4-C10 heterocyclic group and the C1-C10 heteroaryl group each independently has 1 to 3 hetero atoms selected from N, O and S.

The Preparation of Compound of Formula I-b

The present invention also provided a method for the preparation of a representative compound of formula I compound, formula I-b, which comprises the steps:

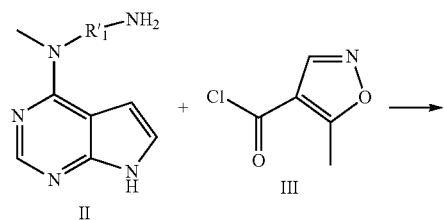

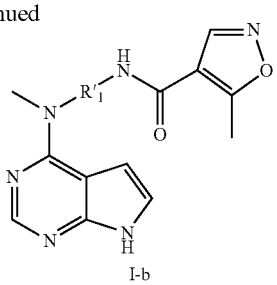

In an inert solvent, reacting formula II compound and formula III compound to obtain formula I-b compound, wherein the R$_1$' is defined as above.

In another preferred embodiment, the inert solvent is selected from the group consisting of dichloromethane, chloroform, 1,2-dichloroethane, toluene, xylene, or the combinations thereof.

In another preferred embodiment, the molar ratio of the formula II compound to the formula III compound is 0.5-2:0.5-2, preferably about 1:1.

In another preferred embodiment, the reaction time of the process is 1-15 h, preferably 2-10 h, more preferably 0.5-5 h.

In another preferred embodiment, the reaction is carried out in the presence of organic base catalyst.

In another preferred embodiment, the organic base catalyst is selected from the group consisting of dimethylaminopyridine (DMAP), diisopropylethylamine (DIPEA), or the combinations thereof.

In another preferred embodiment, the reaction is carried out under the catalyze of acid.

In another preferred embodiment, the acid catalyst is acid-binding agent.

In another preferred embodiment, the acid-binding agent is selected from the group consisting of triethylamine, pyridine, diethylamine, piperidine, or the combinations thereof.

In another preferred embodiment, the method further comprises the step (1-1): dissolving the compound of the formula II, the organic base, and the acid-binding agent in an inert solvent under −50 to 0° C., and dropping the formula III compound for reaction.

In another preferred embodiment, the step further comprises the step (1-2): heating the mixture obtained in the step (1-1) to room temperature for reaction.

In another preferred embodiment, the step further comprises the step (1-3): quenching the reaction with water.

The Preparation of Compound of Formula I-c

The present invention also provided a method for the preparation of a representative compound of formula I compound, formula I-c, which comprises the steps:

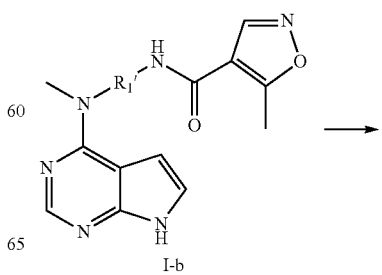

-continued

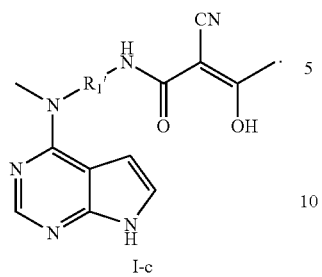

I-c

In an inert solvent, conducting ring-opening reaction to formula I-b compound so as to obtain formula I-c compound, wherein the $R_1'$ is defined as above.

In another preferred embodiment, the inert solvent is selected from the group consisting of toluene, dioxane, THF, or the combinations thereof.

In another preferred embodiment, the reaction is carried out under alkali condition.

In another preferred embodiment, the alkali is selected from the group consisting of potassium carbonate, sodium carbonate, sodium hydrogencarbonate, potassium hydrogencarbonate, or the combinations thereof.

The Use

The diseases which can be treated and/or prevented by compound of formula I of the present invention and the structurally similar compounds include, but are not limited to: autoimmunity or chronic inflammation diseases, such as systemic lupus erythematosus, rheumatoid arthritis, multiple sclerosis, type II diabetes, inflammatory bowel disease, biliary cirrhosis, uveitis and other disfunctions, such as Crohn's disease, ulcerative colitis, bullous pemphigoid, sarcoidosis, psoriasis, psoriatic arthritis, autoimmune myositis, Wegener's granulomatosis, Graves' eye disease, allergies dermatitis and asthma.

The Main Advantages of the Present Invention are:

1. Provided a compound of formula I.

2. Provided a structurally novel specific immune response inhibitor, a preparation method and application thereof.

3. Provided a pharmaceutical composition for the treatment of diseases associated with JAK kinase.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, parts and percentage are weight parts and weight percentage.

The experimental materials and reagents used in the following examples are available from commercially available sources unless otherwise specified.

Example 1 Preparation of Compound 1: N-Methyl-N-(7H-pyrrolo[2,3-d]pyrimidin-4-yl)phenyl-1,4-diamine

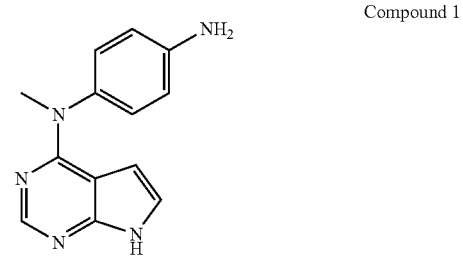 [SMILES: CN(c1ccc(N)cc1)c1ncnc2[nH]ccc12]

Compound 1

1.53 g of 4-chloropyrrolopyrimidine, 4.6 g of N-methyl-p-nitroaniline, 4 M HCl in dioxane solution were weighed in 40 mL of dioxane at 130° C. overnight. The mixture was cooled to room temperature and vacuum concentrated to dry. The residue was slurried with EtOAc until most of the N-methyl-p-nitroaniline disappeared, and the obtained solid was dissolved in methanol and triethylamine (1.5 eq), added with silica gel, and vacuum concentrated to dry under reduced pressure. The residue was chromatographed on silica gel, eluted with dichloromethane/methanol=30/1 system to provide 1.4 g of N-methyl-N-(4-nitrophenyl)-7H-pyrrolo[2,3-d]pyrimidin-4-amine, yield 91.5%.

11 g of the above product and 10% Pd/C was stirred in a methanol closed system equipped with a hydrogen balloon until the reaction of the starting material was completed. The system was filtered, and the filtrate was vacuum concentrated to dryness under reduced pressure, and the residue was purified by pulping with methanol to give the product compound 8g, of which the yield is 72.7%.

The structures of Compound 2 and Compound 3 are as shown in the following Formula I-b:

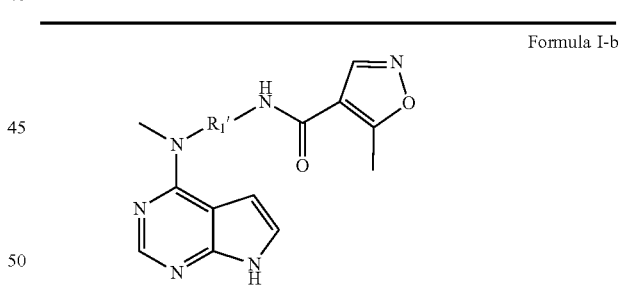

Formula I-b

| Example | Structure | $R_1'$ |
|---------|-----------|--------|
| 2 | formula I-b | phenyl |
| 3 | Formula I-b | Cyclohexyl |

Example 2 Preparation of Compound 2: 5-methyl-isoxazole-{4-methyl-(7H-pyrrolo[2,3-d]pyrimidin-4-yl)-amino]-phenyl}-4-amide 100 mg N-methyl-N-(7H-pyrrolo[2,3-d]pyrimidin-4-)phenyl-1,4-diamine, 16 mg DMAP was weighed in a three-necked flask, and the mixture was stirred and dissolved in 20 mL of dichloromethane, cooled to about −20° C., and 100 mg of triethylamine was added dropwise to the reaction mixture. Then, 103 mg of 5-methylisoxazole-4-carbonyl chloride was slowly added dropwise to a 5 mL dichloromethane solution. After the addition was finished, the reaction was slowly warmed to room temperature naturally and reacted for 5 h, and the reaction was monitored to have been finished by TLC. The reaction was quenched by adding 20 mL of water, and the mixture was separated and extracted and washed three times with dichloromethane. The organic phase was combined, dried over anhydrous Na₂SO₄, and purified by silica gel column chromatography and eluted with ethyl acetate/hexane=1/1 system to provide 72 mg of product, yield 72%.

Example 3 Preparation of Compound 3: 5-methyl-isoxazole-{4-methyl-(7H-pyrrolo[2,3-d]pyrimidin-4-yl)-amino]-cyclohex yl}-amine 100 mg N-methyl-N-(7H-pyrrolo[2,3-d]pyrimidin-4-)phenyl-1,4-diamine, 16 mg DMAP was weighed in a three-necked flask, and the mixture was stirred and dissolved in 20 mL of dichloromethane, cooled to about −20° C., and 100 mg of triethylamine was added dropwise to the reaction mixture. Then, 103 mg of 5-methylisoxazole-4-carbonyl chloride was slowly added dropwise to a 5 mL dichloromethane solution. After the addition was finished, the reaction was slowly warmed to room temperature naturally and reacted for 5 h, and the reaction was monitored to have been finished by TLC. The reaction was quenched by adding 20 mL of water, and the mixture was separated and extracted and washed three times with dichloromethane. The organic phase was combined, dried over anhydrous Na₂SO₄, and purified by silica gel column chromatography and eluted with ethyl acetate/hexane=1/1 system to provide 64 mg of product, yield 64%.

The structures of Compound 4 and Compound 5 are as shown in the following Formula I-c:

Formula I-c

| Example | Structural formula | R₁' |
|---|---|---|
| 4 | Formula I-c | phenyl |
| 5 | Formula I-c | Cyclohexyl |

Example 4 Preparation of Compound 4: 2-cyano-3-hydroxy-2-butene-{4-[methyl-(7H-pyrrolo[2,3-d]pyrimidin-4-yl)-amino]-phenyl}-amide 100 mg of compound 2 was weighed in a three-necked flask, and 30 mL of methanol was added and stirred to dissolve. The mixture was cooled to 0° C., and slowly added with 1 mL saturated sodium bicarbonate solution. After the addition was completed, the mixture was stirred to react at this temperature for 4 h. The reaction was monitored to have been ended by TLC. Methanol was removed by reduced pressure distillation, and 20 mL of water was added. The mixture was separated and extracted and the aqueous phase was washed three times with dichloromethane. The organic phase was combined, dried over anhydrous Na₂SO₄, and purified by silica gel column chromatography and eluted with ethyl dichloromethane/methanol=20/1 system to provide 47 mg of product, yield 47%.

Example 5 Preparation of Compound 5: 2-cyano-3-hydroxy-2-butene-{4-[methyl-(7H-pyrrolo[2,3-d]pyrimidin-4-yl)-amino]-cyclohexyl]-amide 100 mg of compound 3 was weighed in a three-necked flask, and 30 mL of methanol was added and stirred to dissolve. The mixture was cooled to 0° C., and slowly added with 1 mL saturated sodium bicarbonate solution. After the addition was completed, the mixture was stirred to react at this temperature for 4 h. The reaction was monitored to have been ended by TLC. Methanol was removed by reduced pressure distillation, and 20 mL of water was added. The mixture was separated and extracted and the aqueous phase was washed three times with dichloromethane. The organic phase was combined, dried over anhydrous Na₂SO₄, and eluted with ethyl dichloromethane/methanol=20/1 system to provide 52 mg of product, yield 52%.

Example 6 Preparation of Compound 6: 3-Hydroxy-2-(1-{4-[methyl-(7H-pyrrolo[2,3-d]pyrimidin-4-yl)-amino]-iminophenyl}-ethyl)-2-butenenitrile

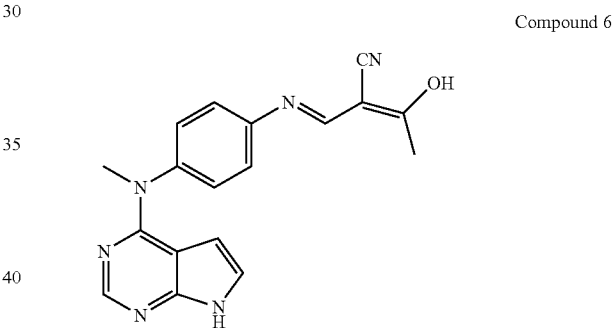

Compound 6

1 g of compound 5, 1 g of 1-(5-methyl-4-isoxazole)-1-ethanone, 25 mL of DMF were weighed and heated at 150° C. for 5 h. 75 mL of water was added dropwise, stirred for 1 h, filtered, and the filter cake was dissolved in dichloromethane/methanol system, and dried over Na₂SO₄, separated by silica gel column chromatography, methylene chloride/methanol=60:1 to give 0.9 g product, yield: 90%.

Example 7 Selective Inhibition of JAK1-3 Enzyme Activity by Compounds of the Present Invention The tested compounds were dissolved in DMSO to provide a 10 mM mother solution. The compound was diluted to 1 mM in DMSO before use, and was gradient diluted by 3 folds to altogether 11 concentrations. After the buffer was prepared, JAK1, JAK2, JAK3 and the substrate were mixed with pre-diluted compounds in different concentrations, and allowed to stand at room temperature for 30 minutes, while each concentration was duplicated for twice. ATP was added and reacted at room temperature for 90 minutes, and antibody was added for detection after the reaction was completed. After incubated for 60 minutes at room temperature, the data was collected by Envision detection, as shown in Table 1.

TABLE 1

JAK enzyme selectivity of Compounds

| | Selectivity fold | |
|---|---|---|
| No. | JAK2/JAK1 IC50 ratio | JAK3/JAK1 IC50 ratio |
| Compound 1 | 7 | 2 |
| Compound 2 | >10 | >10 |
| Compound 3 | >10 | >10 |
| Compound 4 | 7 | 5 |
| Compound 5 | >10 | >10 |
| Compound 6 | >10 | >10 |
| Tofatinib | 2 | <1 |

Example 8 Inhibitory Ability of the Compound of the Present Invention on Proliferation of Mouse Spleen Cells Induced by Mitogen ConA and CD3/CD28 Antibodies CD3 and CD28 monoclonal antibodies can specifically bind to CD3 and CD28 on the surface of T cells, which leads to cross-linking of T cell TCR-CD3 complex, and induces T cell activation and proliferation without the aid of a second signal. This process is similar to antigen-induced T cell activation.

CD3/CD28 antibody-induced inhibition of mouse spleen cell proliferation: 100 uL of cell suspension per well, i.e. $5*10^5$/well, with or without 50 uL of ConA at a concentration of 2.5 ug/uL as well as 50 uL inhibitors at a different concentration, while the negative control wells were supplemented with 50 uL of complete 1640 medium. After 48 hours of culture, the cell culture supernatant was collected for 100 uL/well for subsequent ELISA, and 10 uL/well of CCK8 reagent was added to detect the cell proliferation. The proliferation of immune cells was microscopic observed in each group.

Mitogen ConA-induced inhibition of mouse spleen cell proliferation: Aseptically prepared C57BL/6 mouse spleen cells were adjusted to a cell concentration of $5*10^6$/mL in complete 1640 medium, and 100 uL cell suspension was added to each well of the pre-coated plate with CD3 5 ug/mL, i.e., $5*10^5$/well, and then added with or without 50 uL of CD28 at a concentration of 8 ug/mL, as well as 50 uL of different concentrations of inhibitor (compound 1-6) while negative control well was supplemented with 50 uL of complete 1640 medium. After 144 hours of culture, the cell culture supernatant was collected for 100 uL/well for subsequent ELISA, and 10 uL/well of CCK8 reagent was added to detect the cell proliferation. The proliferation of immune cells was microscopic observed in each group, and the EC50 value was calculated.

The inhibition results of each compound of proliferation of mouse spleen cells induced by mitogen ConA and CD3/CD28 antibodies are shown in Table 2:

TABLE 2

Inhibition activity (EC50) of mouse spleen cells induced by mitogen ConA and CD3/CD28 antibodies of the present invention

| Number of the compound | ConA induction (μM) | CD3/CD28 (μM) |
|---|---|---|
| 1 | 53.88 | 22.73 |
| 2 | 40.34 | 15.09 |
| 3 | 90.71 | 65.67 |
| 4 | 61.22 | 30.85 |
| 5 | >200 | >100 |
| 6 | 93.34 | 52.79 |
| Control compound (A771726) | >200 | >200 |

With ConA as the stimuli, compounds 1, 2, and 3 began to inhibit lymphocyte proliferation at a concentration of 10 uM. As the concentration increased, the inhibitory effect was more pronounced. While the compound 4 showed some inhibition effect only at concentrations of 100 and 200 uM.

Anti-CD3/CD28 was used as the stimuli. Compounds 1 and 3 began to inhibit lymphocyte proliferation at 10 uM concentration, and the inhibitory effect increased significantly with the increase of concentration. Compound 2 began to show lymphocyte proliferation inhibition at 50 uM concentration, but the inhibitory effect increased sharply with increase of concentration; while Compound 4 began to inhibit lymphocyte proliferation at 50 uM, the inhibitory effect increased slowly with the increase of concentration, suggesting that maintaining the isoxazole ring and position $R_1$ as a phenyl group is more advantageous.

The results of this experiment show that compounds 1, 3 mainly inhibit specific immunity, while the inhibition to the non-specific immunosuppression induced by mitogen is weak. For most autoimmune diseases, specific immune (humoral and cellular immune) disorders play an important role in the development of the disease, and inhibiting specific immune responses and correcting specific immune disorders can block the progression and deterioration of diseases.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A compound of Formula I:

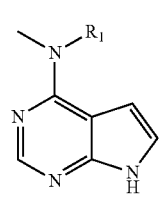

Formula I or a pharmaceutically acceptable salt, stereoisomer, or tautomer thereof,
wherein:
$R_1$ is —$R_{1'}$—$NR_cC(O)R_b$ or —$R_{1'}$—N=$CR_bR_c$;
$R_{1'}$ is cyclohexylene or phenylene;
$R_b$ is $C_2$-$C_8$ alkenyl or $C_1$-$C_{10}$ heteroaryl;
  wherein the $C_1$-$C_{10}$ heteroaryl contains 1, 2, or 3 heteroatoms independently selected from the group consisting of N, O, and S; and
  wherein the $C_2$-$C_8$ alkenyl or $C_1$-$C_{10}$ heteroaryl is substituted with one or more substituents independently selected from the group consisting of halogen, CN, $C_1$-$C_4$ alkyl, $C_1$-$C_4$ haloalkyl, $NH_2$, $NO_2$, and OH; and $R_c$ is H or $C_1$-$C_3$ alkyl.

2. The compound of claim 1, or a pharmaceutically acceptable salt, stereoisomer, or tautomer thereof, wherein $R_b$ is substituted with one or more substituents independently selected from the group consisting of halogen, CN, $C_1$-$C_4$ alkyl, and OH.

3. The compound of claim 1, wherein the compound is of Formula I-b or Formula I-c:

Formula I-b

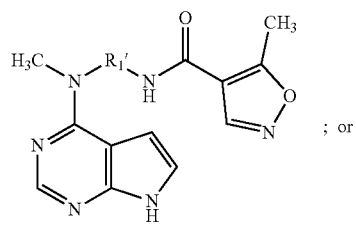

; or

Formula I-c

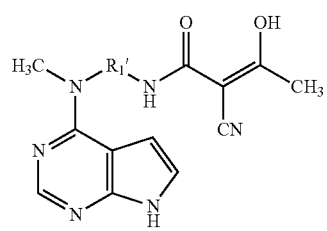

, or a pharmaceutically acceptable salt, stereoisomer, or tautomer thereof.

4. The compound of claim 1, wherein the compound is selected from the group consisting of:

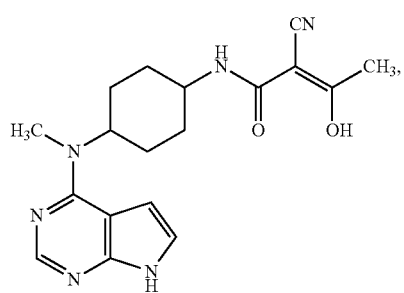

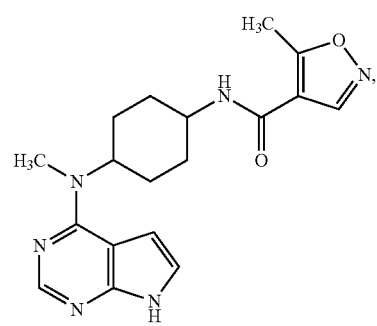

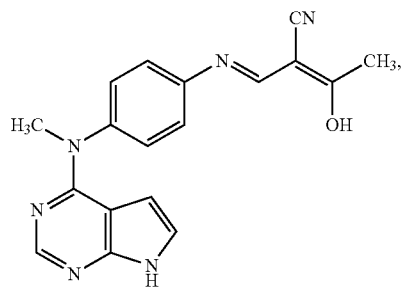

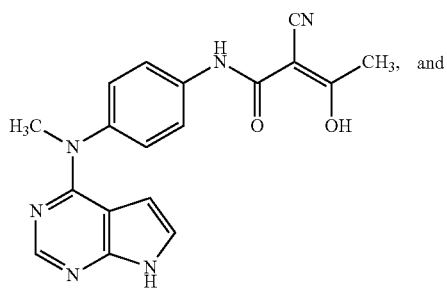

and

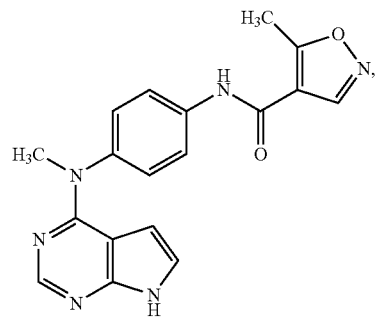

or a pharmaceutically acceptable salt, stereoisomer, or tautomer thereof.

5. A pharmaceutical composition comprising a pharmaceutically acceptable excipient and a therapeutically effective amount of at least one compound of claim 1, or a pharmaceutically acceptable salt, stereoisomer, or tautomer thereof.

6. A method for the non-therapeutic inhibition of Janus kinase activity in a cell, wherein the method comprises contacting the cell with at least one compound of claim 1, or a pharmaceutically acceptable salt, stereoisomer, or tautomer thereof.

7. A process for preparing a compound of Formula I-b of claim 3:

Formula I-b

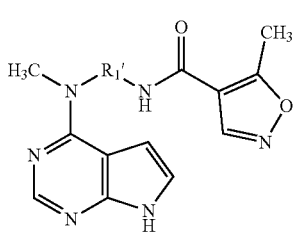

wherein:

R$_{1'}$ is cyclohexylene or phenylene;

wherein the process comprises the following step:

reacting a compound of Formula II:

Formula II wherein:

R$_{1'}$ is cyclohexylene or phenylene;

with a compound of Formula III:

Formula III in the presence of an inert solvent selected from the group consisting of dichloromethane, chloroform, 1,2-dichloroethane, toluene, and xylene, or a combination thereof, to obtain the compound of Formula I-b above.

8. The process of claim 7, wherein the molar ratio of the compound of Formula II to the compound of Formula III is 0.5-2.0:0.5-2.0.

9. The process of claim 8, wherein the molar ratio of the compound of Formula II to the compound of Formula III is 1.0:1.0.

10. A process for preparing a compound of Formula I-c of claim 3:

Formula I-c wherein:

R$_{1'}$ is cyclohexylene or phenylene;

wherein the process comprises the following step:

reacting a compound of Formula I-b:

Formula I-b wherein:

R$_{1'}$ is cyclohexylene or phenylene;

with an alkali selected from the group consisting of sodium bicarbonate, potassium bicarbonate, potassium carbonate, and sodium carbonate, or a combination thereof, in the presence of an inert solvent selected from the group consisting of toluene, dioxane, and teterahydrofuran, or a combination thereof, to obtain the compound of Formula I-c above.

* * * * *